United States Patent [19]

Mikkelsen et al.

[11] Plant 4,743

[45] Jun. 16, 1981

[54] BEGONIA PLANT

[75] Inventors: James C. Mikkelsen; Cornelis P. van den Berg, both of Ashtabula, Ohio

[73] Assignee: Mikkelsens Inc., Ashtabula, Ohio

[21] Appl. No.: 133,901

[22] Filed: Mar. 25, 1980

[51] Int. Cl.[3] ..... A01H 5/00

[52] U.S. Cl. ..... Plt./68

[58] Field of Search ..... Plt/68

*Primary Examiner*—Robert E. Bagwill

*Attorney, Agent, or Firm*—Schwartz, Jeffery, Schwaab, Mack, Blumenthal & Koch

[57] ABSTRACT

A begonia plant known by the cultivar name Ballet having clear yellow flowers and dark green foliage; double flowers, with the tepals in the center being relatively small and ruffled and the outside tepals being relatively large thereby giving the impression of a flower having a relatively small center enframed by the two outside tepals.

1 Drawing Figure

1

The present invention relates to a new and distinctive cultivar of begonia plant, botanically known as *Begonia-×hiemalis Fotsch,* hereinafter referred to by the cultivar name Ballet.

The new cultivar was discovered by me as a mutation of Baluga, disclosed in U.S. Plant Pat. No. 4,127, granted Oct. 18, 1977.

Asexual reproduction by leaf cuttings taken in Ashtabula, Ohio has confirmed that the unique characteristics of the new cultivar are reproduced true to form through successive propagations.

The following characteristics distinguish Ballet from both its parent and other begonias commercially known and used in the floriculture industry;

1. In comparison to the parental cultivar Baluga, the new cultivar has slightly smaller flowers.

2. Flowers are double, with the tepal in the center of the flower being smaller and more ruffled than those of Baluga.

3. The two outside tepals are significantly larger than the center tepals, giving the impressing of a flower having a relatively small center, enframed by the two outside tepals.

4. Flowers are clear yellow, pleasantly contrasting with the dark green foliage.

5. Except for flower form and flower color, the characteristics of Ballet are similar to those of Baluga. These similar characteristics include growth habit, foliage size and shape, rooting habit, regeneration ability from leaf cuttings, resistance to powdery mildew, floriferousness and keeping quality of the flowers.

The accompanying colored photograph clearly illustrates the overall appearance of the new cultivar, and shows the colors as true as it is reasonably possible to obtain in a colored reproduction of this type.

The following is a detailed description of my new begonia cultivar based on plants produced under commercial practices in the greenhouses of Mikkelsens Inc., Ashtabula, Ohio. Color references are made to the Royal Horticultural Society Colour Chart except where general color terms of ordinary dictionary significance are used.

Parentage: The new cultivar is a mutation of the cultivar Baluga.

Propagation:

(A) *Type cutting.*—Generally leaf cuttings.

2

(B) *Time to root.*—3 to 4 weeks at a growing medium temperature of 21° C.

(C) *Rooting habit.*—Abundant, fine, fibrous.

(D) *Time for shoot development.*—9 weeks in summer to 13 weeks in winter, to obtain shoots of approximately 4–5 cm. in length.

Plant description:

(A) *Form.*—Basically upright, close internoded. Growing and scheduling practices can be controlled to result in a medium size plant in a 13 cm. pot or a relatively larger plant grown in a 20 cm. pot.

(B) *Habit of growth.*—Rate of growth moderate for this type of begonia. Generally vegetative shoots are formed at the basal nodes and flowers at the higher nodes.

(C) *Foliage.*—Leaves simple, alternate, borne on strong petioles, 5 mm. in diameter when full grown. Petioles have very fine, short hairs. (1) Size: varying as to the position on the plant and the environmental conditions, with the foliage being up to 11×14 cm. when full grown. (2) Shape: ovate to nearly round. (3) Texture: glabrous, leathery. (4) Margin: crenate to dentate. (5) Color: young foliage top side, yellow-green 147A, interveinal areas infused with red, under side green 138B, interveinal areas heavily infused with Red 46A, mature foliage top side, yellow-green 147A, under side green 138 B-C, interveinal areas infused with red. (6) Venation: 6–7 veins.

Flowering description:

(A) *Flowering habits.*—Flowers in monochasial cymes, with flowers opening up in sequence. Generally each cyme will bear up to nine flowers, frequently less.

(B) *Natural flowering season.*—Year round. However, the plant will flower in an earlier stage of development under short day conditions.

(C) *Flower bud description.*—Flat, ovate, measuring 16×24 mm. Very immature buds are yellow 4D, color jsut before opening yellow 6D; under high light conditions very slightly infused with red.

(D) *Flowers borne.*—On strong, upright peduncles, yellow-green 147B, 5 mm. in diameter at the base; with continued development of the cyme, peduncle bends down, generally at the third flower of the cyme.

(E) *Quantity.*—Except for the basal nodes of every shoot, one peduncle is formed in every leaf axis, with up to nine flowers per peduncle, overall very floriferous.

(F) *Tepals.*—(1) Shape: Outer tepal ovate to nearly round when full grown; center tepals heart-shaped. (2) Color: top side in winter when opening, outer tepals yellow 8A, center tepals yellow 9A, with base yellow 13A, slightly fading to yellow 6C; under side yellow 8B. (3) Number of tepals: Average of 20. (4) Size of tepals: outer two 25×32 mm.; center tepals up to 20 mm. in diameter. (5) Flower size: 40 mm. in diameter when full grown.

(G) *Reproductive organs.*—None observed to date.

Disease resistance:

Resistance to powdery mildew is the same as that of Baluga.

We claim:

1. A new and distinct cultivar of begonia plant known by the cultivar name Ballet, as described and illustrated, and particularly characterized as to uniqueness by the combined characteristics of clear yellow flowers and dark green foliage; double flowers, with the tepals in the center being smaller and more ruffled than those of the parent cultivar Baluga, and by its significantly larger outside tepals, giving the impression of a flower having a relatively small center enframed by the two outside tepals.

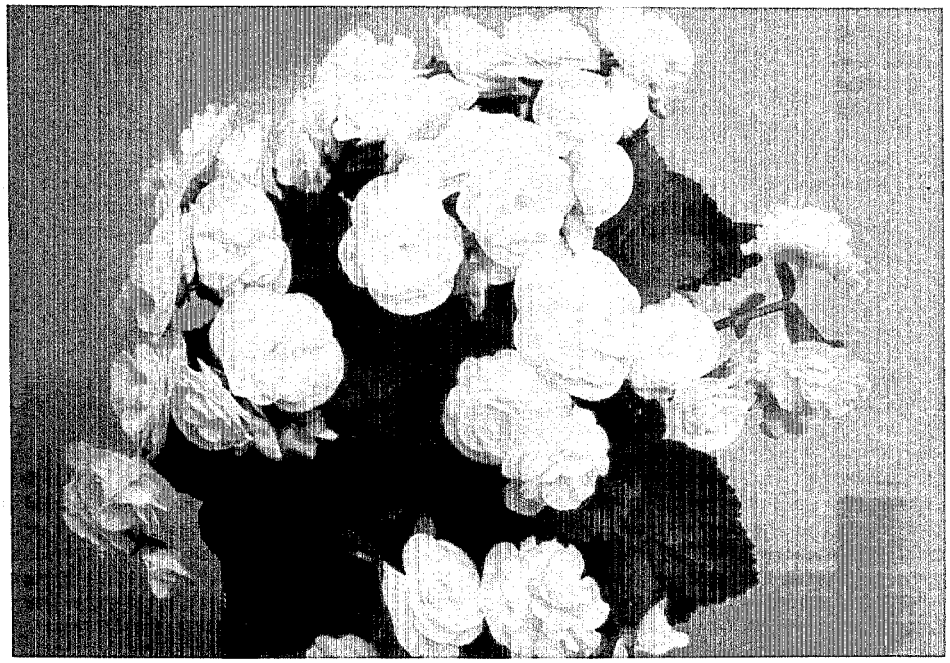

* * * * *